United States Patent [19]

Buschhaus et al.

[11] Patent Number: 4,465,836

[45] Date of Patent: Aug. 14, 1984

[54] DIISOCYANATES

[75] Inventors: Hans-Ulrich Buschhaus, Cologne; Kurt Findeisen, Odenthal; Manfred Bock, Leverkusen, all of Fed. Rep. of Germany

[73] Assignee: Bayer Aktiengesellschaft, Leverkusen, Fed. Rep. of Germany

[21] Appl. No.: 456,901

[22] Filed: Jan. 10, 1983

[30] Foreign Application Priority Data

Jan. 23, 1982 [DE] Fed. Rep. of Germany ....... 3202101

[51] Int. Cl.³ ............................... C07F 7/10
[52] U.S. Cl. .................................... 548/110
[58] Field of Search ........................... 548/110

[56] References Cited

U.S. PATENT DOCUMENTS 3,320,184 5/1967 Fink ........................ 260/2
3,912,754 10/1975 Findeisen et al. ............ 548/307

OTHER PUBLICATIONS

Journal of Organometallic Chemistry (1979) 169, pp. 171–184, Inaba et al., "Reaction of Trimethylsilyl Cyanide with Isocyanates and Carbodiimides".

*Primary Examiner*—Richard Raymond
*Attorney, Agent, or Firm*—Gene Harsh; Joseph C. Gil; Thomas W. Roy

[57] ABSTRACT

Diisocyanates corresponding to the general formula

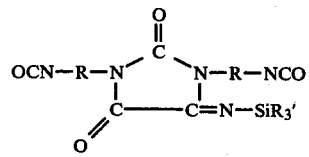

wherein
R denotes the residue of an aliphatic, cycloaliphatic or aromatic diisocyanate and
R' denotes an alkyl group, and a process for the preparation of these diisocyanates by the reaction of a trialkylsilyl cyanide with at least 2 mol of an organic diisocyanate at $-25°$ C. to $200°$ C.

4 Claims, No Drawings

DIISOCYANATES

BACKGROUND OF THE INVENTION

1. Field of the Invention

The present invention is directed to new diisocyanates and to a process for their preparation from diisocyanates and trialkylsilyl cyanides.

2. Description of the Prior Art

The new diisocyanates according to the invention advantageously differ from the most structurally similar diisocyanates according to German Offenlegungsschrift No. 2,329,300 by the fact that they do not undergo any further reactions accompanied either by splitting off of physiologically harmful decomposition products (in the case of the diisocyanates according to German Offenlegungsschrift No. 2,329,300 there is the possibility of decomposition with reversion to the diisocyanate used as starting material and hydrocyanic acid) or by chemical addition of the diisocyanates to mixtures of di- and triisocyanates. The diisocyanates according to the invention constitute a new class of stable diisocyanates which have a substantially lower vapor pressure than the simple diisocyanates used for their preparation.

Although it was already known from J. Organomet. Chem., 169 (1979), 171–184 that trialkylsilylcyanides react with organic monoisocyanates to form imidazolidine diones, it could not be concluded from this prior publication, which deals exclusively with the reaction between monoisocyanates and trialkylsilylcyanides, that the diisocyanates according to the invention would be obtainable by the process according to the invention.

SUMMARY OF THE INVENTION

The present invention relates to diisocyanates corresponding to the general formula

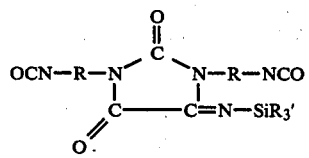

wherein

R denotes an aliphatic hydrocarbon group having 2–12 carbon atoms, cycloaliphatic hydrocarbon group having 4–15 carbon atoms, aromatic hydrocarbon group having 6–15 carbon atoms or araliphatic hydrocarbon group having 7–15 carbon atoms each of which may be optionally halogen substituted, $C_1$–$C_4$-alkyl substituted, methoxy substituted, nitro substituted, $C_1$–$C_4$-alkoxycarbonyl substituted or nitrile group substituted, or a group such as is obtained by removal of the isocyanate groups from a difunctional prepolymer with a maximum molecular weight of about 600 containing isocyanate end groups, and R' denotes an alkyl group.

The present invention also relates to a process for the preparation of these diisocyanates, which is characterized in that 1 mol of trialkylsilyl cyanide corresponding to the formula $$N\equiv C-SiR_3'$$

is reacted with at least 2 mol of an organic diisocyanate of the formula $$R(NCO)_2$$

at about $-25°$ C. to $200°$ C., wherein R and R' have the meaning indicated above.

DETAILED DESCRIPTION OF THE INVENTION

The diisocyanates used for the process according to the invention may be any organic diisocyanates corresponding to the general formula $R(NCO)_2$ wherein R has the meaning already mentioned above and preferably denotes a cycloaliphatic hydrocarbon group having 10 to 15 carbon atoms, a xylylene group or an optionally $C_1$–$C_4$ alkoxycarbonyl substituted aliphatic hydrocarbon group having 4 to 11 carbon atoms. Examples of preferred diisocyanates to be used include tetramethylene diisocyanate, hexamethylene diisocyanate, 1,11-diisocyanatoundecane, 4,4'-dicyclohexyldiisocyanate, bis-(4-isocyanatocyclohexyl)-methane, m- and p-xylylene diisocyanate, 1-isocyanato-3,3,5-trimethyl-5-isocyanatomethylcyclohexane(isophorone diisocyanate), trimethyl-hexamethylene diisocyanate and the methyl, ethyl and butyl esters of 2,6-diisocyanatocaproic acid. Diisocyanates which are less preferred but nevertheless suitable as starting materials according to the invention include difunctional isocyanate prepolymers with a maximum molecular weight of about 600 which may be obtained in known manner, for example, by reaction of the simple diisocyanates exemplified above with sub-equivalent quantities of alkanediols optionally containing ether bridges. A typical example of such a diisocyanate would be the reaction product of hexamethylene diisocyanate with 1,4-dihydroxybutane obtained by observing the NCO/OH equivalent ratio of 2:1.

If desired, aromatic diisocyanates may, of course, also be used or included in the process according to the invention if the products of the process are not required to be lightfast.

The following are examples of suitable aromatic diisocyanates: 1-methylbenzene-2,4-diisocyanate, 1-methylbenzene-2,6-diisocyanate, commercial tolylene diisocyanate mixtures, m- and p-phenylenediisocyanate, naphthylene diisocyanate, diphenylmethane diisocyanate, di- and tri-isopropylbenzene diisocyanates, 1-(isocyanatophenyl)-ethyl isocyanate as well as diisocyanates carrying various substituents, e.g. alkoxy-, nitro-, chloro- or bromo-substituted diisocyanates. Any mixtures of the diisocyanates mentioned above as examples may, of course, be used in the process according to the invention.

The compounds with which the diisocyanates are reacted in the process according to the invention are trialkylsilyl cyanides corresponding to the formula $$N\equiv C-SiR_3'$$

wherein R' has the meaning already indicated and preferably denotes a $C_1$–$C_4$-alkyl group, in particular a methyl group.

The process according to the invention is carried out in the temperature range of from about $-25°$ C. to $200°$ C., preferably from about $25°$ C. to $180°$ C., optionally in the presence of suitable catalysts, e.g. Lewis acids such as aluminum chloride or iron(III) chloride and/or in the presence of suitable solvents. The process according to the invention may, for example, be carried out by introducing the reaction components into the reaction vessel as a mixture and starting the reaction by heating.

The process could also be carried out, for example, by introducing the diisocyanate into the reaction vessel at an elevated temperature and subsequently adding the trialkylsilyl cyanide.

The process according to the invention is generally carried out using from 2 to about 50 mol, preferably from about 5 to 15 mol of diisocyanate per mol of trialkylsilyl cyanide. The end of the reaction between trialkylsilyl cyanide and diisocyanate may be detected, for example, by cessation of the reflux of trialkylsilyl cyanide or it may be determined by titration of the remaining isocyanate content.

If desired, unreacted diisocyanate may be removed at the end of the reaction, for example by thin layer distillation or rotary distillation or by extraction with solvents such as cyclohexane, hexane or petroleum ether but for many of the fields of application mentioned hereinafter the new polyisocyanates may suitably be used in the form of their solutions in the unreacted diisocyanates used as starting compounds.

At elevated temperatures, the formation of polyisocyanates containing uretdione or isocyanurate groups is also to be expected. If the formation of these by-products is undesirable, it is advisable to carry out the process according to the invention at low temperatures ranging from about 25° C. to 120° C. and to heat the reaction mass to this temperature range during a period of about 300 to 420 minutes.

If these precautions are observed, the products obtained after removal of the excess diisocyanate used as starting material contain at least about 70%, preferably at least about 90% of the diisocyanates corresponding to the general formula indicated above.

The process according to the invention may be carried out solvent-free or in the presence of an inert organic solvent. Suitable inert solvents include e.g. aliphatic and cycloaliphatic hydrocarbons; halogenated hydrocarbons such as methylene chloride, chloroform and di- and tri-chloroethylene; aromatic solvents such as benzene, toluene and xylene; halogenated aromatic solvents such as chlorobenzene, dichlorobenzene and trichlorobenzene; dioxane; ethyl acetate; ethyl glycol acetate; acetone; acetonitrile; dimethylformamide; and mixtures of these solvents.

The new polyisocyanates with a 5-trialkylsilyl-imino-imidazolidine dione structure according to the invention constitute a new class of organic polyisocyanates. The fact that the compounds have the general structure indicated above is clear from molecular weight determinations as well as from the data obtained from infra-red (Macromol. Chem. 78 191 (1964)), nuclear resonance and mass spectroscopy data. The new compounds are suitable as intermediate products for the production of plant protective agents and in particular they are valuable starting compounds for the production of polyurethanes. Polyisocyanates according to the invention which have aliphatically bound isocyanate groups in particular are valuable starting compounds for the production of lightfast polyurethane lacquers and foils. The new polyisocyanates are readily soluble in the usual lacquer solvents and have good pigment compatibility. Another of their characteristics which is of the greatest practical importance is that they have a much lower vapor pressure than the corresponding diisocyanates from which they were prepared, and consequently are also physiologically harmless.

EXAMPLES

EXAMPLE 1

5-Trimethylsilylimino-N,N'-di-(isocyanatoisophoryl)-imidazolidine dione 666 g (3 mol) of isophorone diisocyanate are mixed with 29.7 g (0.3 mol) of trimethylsilyl cyanide and the mixture is stirred for 0.5 hours at 130° C. and 4 hours at 160° C. and subjected to thin layer evaporation in a stream of nitrogen at 180° C./0.1 Torr. Yield: 143.8 g (88.3% of theoretical yield) of a yellow oil which solidifies to a vitreous mass at 56° C.

IR=2250 cm$^{-1}$: NCO
1790, 1740 cm$^{-1}$: C=O
1680 cm$^{-1}$: C=N
1260, 850 cm$^{-1}$: Si

Isocyanate content calculated: 15.5%, found: 14.9%.

EXAMPLE 2

5-Trimethylsilylimino-N,N'-di-(6-isocyanatohexyl)-imidazolidine dione 3360 g (20 mol) of 1,6-diisocyanatohexane are mixed with 198 g (2 mol) of trimethylsilyl cyanide, stirred for 30 minutes at 120° C. and 2 hours at 160° C. and thin layer evaporated in a stream of nitrogen at 180° C./0.1 Torr.

Yield: 846 g (97.2% of theoretical yield) of a light yellow liquid.

Isocyanate content calculated: 19.3%, found: 17.1%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate corresponding to the general formula

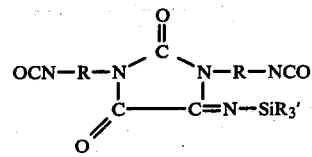

wherein
R denotes an aliphatic hydrocarbon group having 2–12 carbon atoms, cycloaliphatic hydrocarbon group having 4–15 carbon atoms, aromatic hydrocarbon group having 6–15 carbon atoms or araliphatic hydrocarbon group having 7 to 15 carbon atoms each of which may be optionally halogen substituted, C$_1$–C$_4$-alkyl substituted, methoxy substituted, nitro substituted, C$_1$–C$_4$-alkoxycarbonyl substituted or nitrile group substituted, or a group obtained by removal of the isocyanate groups from a difunctional prepolymer with a maximum molecular weight of about 600 containing isocyanate end groups, and
R' denotes an alkyl group.

2. The diisocyanates according to claim 1 wherein
R denotes a cycloaliphatic hydrocarbon group having 10–15 carbon atoms, a xylylene group or optionally $C_1$–$C_4$-alkoxycarbonyl-substituted aliphatic hydrocarbon group having 4–11 carbon atoms and R' denotes a methyl group.

3. The diisocyanate according to claim 1 wherein R denotes hexamethylene.

4. The diisocyanate according to claim 1 wherein R denotes the residue obtained when the isocyanate groups are removed from isophorone diisocyanate.

* * * * *